(12) United States Patent
Sharma et al.

(10) Patent No.: US 11,952,399 B2
(45) Date of Patent: Apr. 9, 2024

(54) METHODS FOR PURIFYING PROTEINS (71) Applicant: AMGEN INC., Thousand Oaks, CA (US)

(72) Inventors: Ashish Sharma, Lincoln, RI (US); Balakumar Thangaraj, Lexington, MA (US)

(73) Assignee: AMGEN INC., Thousand Oaks, CA (US)

( * ) Notice: Subject to any disclaimer, the term of this patent is extended or adjusted under 35 U.S.C. 154(b) by 941 days.

(21) Appl. No.: 16/708,987

(22) Filed: Dec. 10, 2019

(65) Prior Publication Data

US 2020/0190137 A1 Jun. 18, 2020

Related U.S. Application Data (60) Provisional application No. 62/781,257, filed on Dec. 18, 2018.

(51) Int. Cl.
*C07K 1/20* (2006.01)
*C07K 14/715* (2006.01)

(52) U.S. Cl.
CPC ............ *C07K 1/20* (2013.01); *C07K 14/7151* (2013.01); *C07K 2319/30* (2013.01)

(58) Field of Classification Search
None
See application file for complete search history.

(56) References Cited

U.S. PATENT DOCUMENTS

| 5,395,760 A | 3/1995 | Smith et al. |
| 5,610,279 A | 3/1997 | Brockhaus et al. |
| 7,294,481 B1 | 11/2007 | Fung |
| 8,188,242 B2 * | 5/2012 | Gagnon ............ A61K 39/39591 530/390.5 |
| 2014/0316114 A1 * | 10/2014 | Won ................. C07K 14/70578 530/387.3 |
| 2017/0152298 A1 * | 6/2017 | Banerjee .............. B01D 15/424 |
| 2017/0369553 A1 * | 12/2017 | Park ...................... C07K 19/00 |

FOREIGN PATENT DOCUMENTS

WO WO-2016009049 A1 * 1/2016 ....... C07K 14/70578

OTHER PUBLICATIONS

Liu et al. "Recovery and purification process development for monoclonal antibody production" mAbs 2-5, 480-499, 2010 (Year: 2010).*
Sofer, Virus Inactivation in the 1990s—and into the 21st Century, Part 4, Culture Media. Biotechnology Products, and Vaccines, Biopharm International, pp. 50-57 (2003).

* cited by examiner

*Primary Examiner* — Daniel E Kolker
*Assistant Examiner* — James L Rogers
(74) *Attorney, Agent, or Firm* — MARSHALL, GERSTEIN & BORUN LLP (57) ABSTRACT

The invention pertains to methods of purifying fusion proteins, in particular TNFR:Fc fusion proteins. Methods disclosed herein can be used to produce highly pure TNFR:Fc fusion proteins (e.g., etanercept) having a biological activity by removing hard to separate product related impurities such as clipped and/or mis-fold/aggregated TNFR:Fc fusion proteins.

21 Claims, 3 Drawing Sheets
Specification includes a Sequence Listing.

METHODS FOR PURIFYING PROTEINS

CROSS-REFERENCE TO RELATED APPLICATIONS

This application claims benefit to U.S. Provisional Application No. 62/781,257, filed Dec. 18, 2018, the contents of which are incorporated by reference in its entirety.

SUBMISSION OF SEQUENCE LISTING ON ASCII TEXT FILE

The context of the following submission on ASCII text file is incorporated herein by reference in its entirety: a computer readable for (CRF) of Sequence Listing (filed name: A-2333-NP Seq Listing, date created: Dec. 10, 2019, size: 4311 bytes).

FIELD OF THE INVENTION

The present invention relates generally to the purification of recombinant proteins, in particular, tumor necrosis factor receptor (TNFR): Fc fusion proteins.

BACKGROUND OF THE INVENTION

Clinical manufacture of therapeutic proteins is an expensive, large scale endeavor. Therapeutic proteins are typically produced recombinantly in mammalian cells in bioreactors, harvested and then purified using downstream purification processes. These downstream purification processes usually include recovery/capture steps (e.g., affinity chromatography, viral inactivation) followed by polishing purification steps (e.g., various chromatographic steps), along with viral filtration and final concentration steps.

Process and product related impurity removal are important considerations in the design of a robust downstream purification process for therapeutic proteins. Certain product related impurities could be more challenging to remove due to their similarities to the purified product and could be carried forward after polishing chromatography columns to downstream purification steps. Once carried forwarded, such impurities can negatively impact later purification steps as they can reduce the efficiency and throughput of those steps. Purification processes that can remove such impurities earlier can improve the robustness of the overall downstream process.

TNFR:Fc fusion proteins can be prepared by fusing a soluble form of the necrosis factor receptor (TNFR) and an Fc domain of an immunoglobin molecule. Examples of such fusion proteins include a fusion protein of the extracellular ligand-binding portion of the human 75 kilodalton (p75) TNFR and the Fc domain of a human IgG1. Etanercept is a dimer of the p75 TNFR:Fc fusion protein. TNFR:Fc fusion proteins may be produced recombinantly in Chinese hamster ovary (CHO) cells. A commercially available etanercept is known as ENBREL® (etanercept; Immunex Inc., Thousand Oaks, CA), produced in genetically engineered Chinese hamster ovary (CHO) cells.

SUMMARY OF THE INVENTION

The present application discloses methods for purifying fusion proteins, in particular TNFR:Fc fusion proteins. Methods disclosed herein can purify TNFR:Fc fusion proteins from those difficult to remove, product related impurities and advantageously contain one polishing chromatographic step. Methods disclosed herein also produce p75 TNFR:Fc fusion proteins having at least comparable purity and biological activity related to the commercially available etanercept.

In one embodiment, disclosed herein is a method for purifying a tumor necrosis factor receptor (TNFR):Fc fusion protein, comprising: a) subjecting a sample comprising the TNFR:Fc fusion protein and at least one contaminant to a chromatography medium under conditions whereby the TNFR:Fc fusion protein binds to the chromatography medium, b) eluting the TNFR:Fc fusion protein from the chromatography medium, and c) filtering the eluate from b) through one or more viral filtration membranes to obtain the purified TNFR:Fc fusion protein, wherein the chromatography medium comprises a ligand comprising a hydrophobic group. In one embodiment, the TNFR:Fc fusion protein is etanercept.

In one embodiment, the chromatography medium is a hydrophobic interaction chromatography (HIC) medium. In one embodiment, the ligand of the HIC medium is an alkyl group, a phenyl group, an ether group, or a diol group. In one embodiment, the ligand of the HIC medium is an alkyl group selected from a butyl group, a propyl group, an isopropyl group, a pentyl group, a hexyl group, and an octyl group. In one embodiment, the ligand of the HIC medium is a butyl group or a phenyl group. In one embodiment, the HIC medium is composed of hydroxylated methacrylic polymer resins functionalized with a butyl ligand group.

In one embodiment, the chromatography medium comprises a ligand comprising a hydrophobic group and an ionic group. In one embodiment, the hydrophobic group is a phenyl group or a benzyl group, and the ionic group is a strong cation group, a weak cation group, or a combination thereof. In one embodiment, the hydrophobic group is a phenyl group or a benzyl group, and the ionic group is a strong anion group, a weak anion group, or a combination thereof. In one embodiment, the ligand of chromatography medium comprises 1) a benzyl group and an amine group, 2) a phenyl group and a carboxylic group, or 3) a benzyl group, a sulfonic group and a carboxylic group.

In one embodiment of the method, the sample has a salt concentration of from about 0.4 M to about 2 M, in another embodiment, the sample has a pH of from about 5.0 to about 8.5.

In one embodiment of the method, the step b) comprises eluting the TNFR:Fc fusion protein using gradient elution. In one embodiment, the TNFR:Fc fusion protein is eluted using a gradient of: from 100% of a first solution having a salt concentration of from about 0.4 M to about 2 M, to 100% of a second solution having a salt concentration of from 0 mM to about 100 mM. In one embodiment, the first solution has a salt concentration of from about 0.4 M to about 2 M and the second solution has a salt concentration of from 0 mM to about 50 mM. In one embodiment, the first solution comprises a salt selected from ammonium sulfate, ammonium chloride, sodium sulfate, sodium chloride, sodium citrate, sodium acetate, sodium phosphate, potassium sulfate, potassium phosphate, and potassium chloride. In one embodiment, the second solution comprises a salt selected from ammonium sulfate, ammonium chloride, sodium sulfate, sodium chloride, sodium citrate, sodium acetate, sodium phosphate, potassium sulfate, potassium phosphate, and potassium chloride.

In one embodiment, the first and second solutions each has a pH of from about 5.0 to about 8.5, in another embodiment, the first and second solutions have the same pH. In one embodiment, the first and second solutions comprise the same buffer. In one embodiment, the first and second solutions each comprises a phosphate buffer, an acetate buffer, or a citrate buffer. In one embodiment, the first and the second solutions each comprises a buffering agent at a concentration of from about 10 mM to about 200 mM. In one embodiment, the first solution comprises 0.42 M Sodium Citrate, 0.05 M Sodium Phosphate, and a pH of about 6.5, and the second solution comprises 0.05 M Sodium Phosphate, and a pH of about 6.5.

In one embodiment, the eluate from step b) that is subjected to the filtration in step c) comprises less than about 1 wt % of the HIC Peak 3. In one embodiment, the eluate from step b) that is that is subjected to the filtration in step c) further comprises less than about 1 wt % of the HIC Peak 1. In one embodiment, the eluate being filtered in step c) has a protein concentration of from about 2 mg/mL to about 10 mg/mL.

In one embodiment of the method, the pore size of the one or more viral filtration membranes is at or greater than about 15 nm, in another embodiment, the pore size of the one or more viral filtration membranes is from about 20 nm to about 100 nm.

In one embodiment, the one or more viral filtration membranes are polyethersulfone (PES) membranes or polyvinylidene fluoride (PVDF) membranes. In one embodiment, the PES membrane is a hydrophilic asymmetric surface modified PES membrane. In one embodiment, the PVDF membrane is a hydrophilic modified PVDF membrane.

In one embodiment, the method further comprising prefiltering the eluate from step b) prior to step c). In one embodiment, the eluate from step b) is prefiltered using one or more adsorptive depth prefilters, in another embodiment, the eluate from step b) is prefiltered using one or more charged or surface modified microporous membranes. In one embodiment, the one or more adsorptive depth prefilters are composed of diatomaceous earth, cellulose, activated carbon, high capacity diatomaceous earth metals and cellulose, or High capacity polyacrylic fiber and silica. In one embodiment, the one or more charged or surface modified microporous membranes are composed of regenerated cellulose, polyethersulfone, polyarylsulphone, polysulfone, polyimide, polyamide, or polyvinylidenedifluoride.

In one embodiment, the method further comprising one or more purification steps selected from viral inactivation, affinity chromatography, and ultrafiltration and diafiltration.

DETAILED DESCRIPTION OF THE INVENTION

The present invention is based in part on the novel and unexpected demonstration that product related impurities having properties similar to that of the purified product can be removed by methods disclosed herein. It is demonstrated that TNFR:Fc fusion proteins can be purified to high purity by processes containing one polishing chromatographic step.

As used herein, the term "TNFR:Fc fusion protein" refers to a recombinant protein comprising all or part of an extracellular domain of a tumor necrosis factor receptor (TNFR) joined to an Fc domain of an antibody by peptide bonds. "Proteins", which may be used interchangeably with "peptides" or "polypeptides", are also inclusive of modifications including, but not limited to, glycosylation, lipid attachment, sulfation, gamma-carboxylation of glutamic acid residues, hydroxylation and ADP-ribosylation. Proteins may be produced by recombinant animal cell lines using cell culture methods and may be referred to as "recombinant proteins". Recombinant proteins may be produced intracellularly or secreted into the culture medium from which it can be recovered and/or collected.

"TNFR" refers to proteins comprising amino acid sequences that are identical or substantially similar to the sequence of a native mammalian tumor necrosis factor receptor (TNFR). Biological activity for the purpose of determining substantial similarity includes the capacity to bind tumor necrosis factor (TNF), to transduce a biological signal initiated by TNF binding to a cell, or to cross-react with anti-TNFR antibodies raised against TNFR from natural (i.e., non-recombinant) sources. A TNFR may be any mammalian TNFR, including murine or human TNFRs. Such TNFRs are described in U.S. Pat. Nos. 5,395,760 and 5,610,279, which are incorporated by reference herein in its entirety. A particularly preferred TNFR is that described in U.S. Pat. No. 5,395,760, which has an apparent molecular weight by SDS-PAGE of about 80 kilodaltons in its glycosylated form. An extracellular domain includes, but is not limited to, amino acid sequences substantially similar to amino acids 1-163, 1-185, or 1-235 of FIG. 2A of U.S. Pat. No. 5,395,760.

The Fc domain of an antibody includes human or animal immunoglobulin domains $C_{H2}$ and $C_{H3}$ or immunoglobulin domains substantially similar to these. The biological activity of an Fc domain of an antibody for the purpose of determining substantial similarity is the ability to be bound by a second protein that binds to naturally-occurring Fc domain of antibodies, such as Protein A or Protein G. See Charles A Hasemann and J. Donald Capra, Immunoglobulins: Structure and Function, in William E. Paul, ed., Fundamental Immunology, Second Edition, 209, 212-213 (1989).

Examples of TNFR:Fc fusion protein include a fusion protein of an extracellular ligand-binding portion of the human 75 kilodalton (p75) TNFR and an Fc domain of a human IgG1. The human p75 TNFR:Fc fusion protein can form a dimer via disulfate bonds. An example of such a dimer is etanercept. A commercially available etanercept is known as ENBREL®. ENBREL® is produced by recombinant DNA technology in a Chinese hamster ovary (CHO) mammalian cell expression system. It consists of 934 amino acids and has an apparent molecular weight of approximately 150 kilodaltons (Physicians Desk Reference, 2002, Medical Economics Company Inc.). The full sequence expressed in CHO cells is shown below. However, it is to be understood that minor modifications and deletions of this sequence (up to 10%) may be possible and can be used within the scope of the invention. The methods and techniques of the present invention can be used to produce biosimilar etanercept that differs from ENBREL® in, for example, its formulation, dosage, presentation, approved indications or uses, sequence, glycosylation pattern, or other post-translational modification.

1 Leu-Pro-Ala-Gln-Val-Ala-Phe-Thr-Pro-Tyr-
11 Ala-Pro-Glu-Pro-Gly-Ser-Thr-Cys-Arg-Leu-
21 Arg-Glu-Tyr-Tyr-Asp-Gln-Thr-Ala-Gln-Met-
31 Cys-Cys-Ser-Lys-Cys-Ser-Pro-Gly-Gln-His-
41 Ala-Lys-Val-Phe-Cys-Thr-Lys-Thr-Ser-Asp-
51 Thr-Val-Cys-Asp-Ser-Cys-Glu-Asp-Ser-Thr-
61 Tyr-Thr-Gln-Leu-Trp-Asn-Trp-Val-Pro-Glu-
71 Cys-Leu-Ser-Cys-Gly-Ser-Arg-Cys-Ser-Ser-
81 Asp-Gln-Val-Glu-Thr-Gln-Ala-Cys-Thr-Arg-
91 Glu-Gln-Asn-Arg-Ile-Cys-Thr-Cys-Arg-Pro-
101 Gly-Trp-Tyr-Cys-Ala-Leu-Ser-Lys-Gln-Glu-
111 Gly-Cys-Arg-Leu-Cys-Ala-Pro-Leu-Arg-Lys-
121 Cys-Arg-Pro-Gly-Phe-Gly-Val-Ala-Arg-Pro-
131 Gly-Thr-Glu-Thr-Ser-Asp-Val-Val-Cys-Lys-
141 Pro-Cys-Ala-Pro-Gly-Thr-Phe-Ser-Asn-Thr-
151 Thr-Ser-Ser-Thr-Asp-Ile-Cys-Arg-Pro-His-
161 Gln-Ile-Cys-Asn-Val-Val-Ala-Ile-Pro-Gly-
171 Asn-Ala-Ser-Met-Asp-Ala-Val-Cys-Thr-Ser-
181 Thr-Ser-Pro-Thr-Arg-Ser-Met-Ala-Pro-Gly-
191 Ala-Val-His-Leu-Pro-Gln-Pro-Val-Ser-Thr-
201 Arg-Ser-Gln-His-Thr-Gln-Pro-Thr-Pro-Glu-
211 Pro-Ser-Thr-Ala-Pro-Ser-Thr-Ser-Phe-Leu-
221 Leu-Pro-Met-Gly-Pro-Ser-Pro-Pro-Ala-Glu-
231 Gly-Ser-Thr-Gly-Asp-Glu-Pro-Lys-Ser-Cys-
241 Asp-Lys-Thr-His-Thr-Cys-Pro-Pro-Cys-Pro-
251 Ala-Pro-Glu-Leu-Leu-Gly-Gly-Pro-Ser-Val-
261 Phe-Leu-Phe-Pro-Pro-Lys-Pro-Lys-Asp-Thr-
271 Leu-Met-Ile-Ser-Arg-Thr-Pro-Glu-Val-Thr-
281 Cys-Val-Val-Val-Asp-Val-Ser-His-Glu-Asp-
291 Pro-Glu-Val-Lys-Phe-Asn-Trp-Tyr-Val-Asp-
301 Gly-Val-Glu-Val-His-Asn-Ala-Lys-Thr-Lys-
311 Pro-Arg-Glu-Glu-Gln-Tyr-Asn-Ser-Thr-Tyr-
321 Arg-Val-Val-Ser-Val-Leu-Thr-Val-Leu-His-
331 Gln-Asp-Trp-Leu-Asn-Gly-Lys-Glu-Tyr-Lys-
341 Cys-Lys-Val-Ser-Asn-Lys-Ala-Leu-Pro-Ala-
351 Pro-Ile-Glu-Lys-Thr-Ile-Ser-Lys-Ala-Lys-
361 Gly-Gln-Pro-Arg-Glu-Pro-Gln-Val-Tyr-Thr-
371 Leu-Pro-Pro-Ser-Arg-Glu-Glu-Met-Thr-Lys-
381 Asn-Gln-Val-Ser-Leu-Thr-Cys-Leu-Val-Lys-
391 Gly-Phe-Tyr-Pro-Ser-Asp-Ile-Ala-Val-Glu-
401 Trp-Glu-Ser-Asn-Gly-Gln-Pro-Glu-Asn-Asn-
411 Tyr-Lys-Thr-Thr-Pro-Pro-Val-Leu-Asp-Ser-
421 Asp-Gly-Ser-Phe-Phe-Leu-Tyr-Ser-Lys-Leu-
431 Thr-Val-Asp-Lys-Ser-Arg-Trp-Gln-Gln-Gly-
441 Asn-Val-Phe-Ser-Cys-Ser-Val-Met-His-Glu-
451 Ala-Leu-His-Asn-His-Tyr-Thr-Gln-Lys-Ser-
461 Leu-Ser-Leu-Ser-Pro-Gly-Lys

Disclosed herein are methods for purifying TNFR:Fc fusion proteins. TNFR:Fc fusion proteins can be produced by host cells that have been genetically engineered to produce the protein. Methods of genetically engineering cells to produce proteins are well known in the art. See e.g. Ausabel et al., eds. (1990), Current Protocols in Molecular Biology (Wiley, New York). Such methods include introducing nucleic acids that encode and allow expression of the fusion protein into living host cells. These host cells can be bacterial cells, fungal cells, or, preferably, mammalian cells grown in culture. Bacterial host cells include, but are not limited to, *Escherichia coli* cells. Examples of suitable *E. coli* strains include: HB101, DH5α, GM2929, JM109, KW251, NM538, NM539, and any *E. coli* strain that fails to cleave foreign DNA. Fungal host cells that can be used include, but are not limited to, *Saccharomyces cerevisiae*, *Pichia pastoris* and *Aspergillus* cells. Examples of mammalian cell lines that can be used are CHO, VERO, BHK, HeLa, Cos, MDCK, 293, 3T3, and WI138. New mammalian cell lines can be established using methods well known by those skilled in the art (e.g., by transformation, viral infection, and/or selection). Optionally, the protein can be secreted by the host cells into the medium.

In one aspect, disclosed herein is a method for purifying a TNFR:Fc fusion protein, comprising a) subjecting a sample comprising the TNFR:Fc fusion protein and at least one contaminant to a chromatography medium under conditions whereby the TNFR:Fc fusion protein binds to the medium, b) eluting the TNFR:Fc fusion protein from the chromatography medium, and c) filtering the eluate from b) through one or more viral filtration membranes to obtain the purified TNFR:Fc fusion protein, wherein the chromatography medium comprises a ligand comprising a hydrophobic group.

TNFR:Fc fusion proteins that may be purified by the method include any of the TNFR:Fc fusion proteins described above. In certain embodiments, the TNFR:Fc fusion protein is a fusion protein of an extracellular ligand-binding portion of the human 75 kilodalton (p75) TNFR and an Fc domain of a human IgG1. In certain embodiments, the TNFR:Fc fusion protein is etanercept.

In step a) of the methods disclosed herein, a composition comprising the TNFR:Fc fusion protein and at least one contaminant is subjected to a chromatography medium under conditions whereby the TNFR:Fc fusion protein binds to the medium, wherein the chromatography medium comprises a ligand comprising a hydrophobic group.

As used herein, a "contaminant" includes any foreign or objectable molecule, particularly a biological macromolecule such as a DNA, an RNA, or a protein, other than the protein being purified that is present in a sample of a protein being purified. Contaminants include, for example, other proteins from cells that express the protein being purified. When a TNFR:Fc fusion protein is produced by a mammalian cell (e.g., CHO cells) transformed with an expression vector comprising a polynucleotide encoding the TNFR:Fc fusion protein, it is possible that the fusion protein aggregates, and/or mis-folds, and/or dimerizes improperly, and/or is truncated, e.g., due to proteolytic cleavage. Contaminates include truncated and/or mis-folded and/or mis-dimerized and/or aggregated TNFR:Fc fusion protein.

In certain embodiments, the sample comprising a TNFR:Fc fusion protein and at least one contaminant in step a) is a cell culture supernatant comprising a TNFR:Fc fusion protein, or a cell extract comprising a TNFR:Fc fusion protein. In certain embodiments, the sample comparing a TNFR:Fc fusion protein and at least one contaminant is a partially purified cell culture supernatant or a partially purified cell extract comprising a TNFR:Fc fusion protein. A partially purified cell culture supernatant or a partially purified cell extract may be obtained by subjecting a cell culture supernatant or a cell extract comprising a TNFR:Fc fusion protein to earlier purification steps such as affinity chromatography and/or virus inactivation.

In affinity chromatography, a TNFR:Fc fusion protein can be purified by binding to a second protein affixed to a solid support known as an affinity chromatography resin or medium. A sample containing a TNFR:Fc fusion protein can be applied to this resin. The resin can be subsequently washed in a solution that does not interfere with the binding of the second protein to the fusion protein. The fusion protein can thereafter be eluted from the resin with a solution that interferes with the binding of the fusion protein by the second protein.

In certain embodiments, the second protein is a protein that can bind to the Fc domain of the fusion protein. In certain embodiments, the second protein is Protein A, Protein G, or Protein L. Affinity chromatography resins are commercially available from a number of manufacturers including BioRad, Merck, Amersham Pharmacia Biotech, GE Healthcare Life Sciences, Thermo Fischer Scientific, JSR life sciences, Repligen and Millipore Corporation. In certain embodiments, the second protein is Protein A. The Protein A can be native Protein A (e.g., from *Staph. Aureus*), recombinant Protein A or functional variant thereof. Examples of commercially available Protein A resins that may be used include: ProSep®-vA HC, ProSep® Ultra Plus, MabSelect™, MabSelect SuRe™, MabSelect Sure™ LX, MabSelect™ PrismA, MabSelect™ Sure pcc, MabSelect™ Xtra, Amsphere™, CaptivA and other commercially available affinity resins.

Virus inactivation can be achieved by, e.g., using virus inactivating agents and/or methods that render viruses inactive, or unable to replicate or infect. Many virus inactivating agents are known and used in the art. See, e.g., Gail Sofer, "Virus Inactivation in the 1990s—and into the 21st Century, Part 4, Culture Media. Biotechnology Products, and Vaccines," Biopharm International, pp. 50-57 (2003). Exemplary virus inactivation methods include solvent/detergent inactivation (e.g. with Triton X 100): pasteurization (heating); acidic pH inactivation (e.g., at pH 3-5); and ultraviolet (UV) inactivation. It is also possible to combine two or more of these methods, e.g., perform acidic pH inactivation at elevated temperature, to inactivate viruses.

Chromatography media or resins that may be used in step (a) of the method disclosed herein include chromatography media or resins that comprise a ligand comprising a hydrophobic group. In certain embodiments, chromatography medium or resin that may be used in step (a) is a hydrophobic interaction (HIC) medium. A HIC medium is composed of a base matrix coupled to a hydrophobic ligand that can interact with proteins. The hydrophobic ligand may be coupled to the based matrix via a spacer. HIC separates proteins based on a reversible interaction between proteins and the hydrophobic surface of a HIC medium. Common base matrices include, but not limited to, agarose, methacrylate such as a hydroxylated methacrylic polymer, poly (styrene-divinylbenzene) and silica. Exemplary hydrophobic ligands include, but not limited to, alkyl groups, phenyl groups, ether groups, and diol groups. Exemplary alkyl groups include, but not limited to, a butyl group, a propyl group, an isopropyl group, a pentyl group, a hexyl group, and an octyl group. HIC media having the above described ligands are commercially available, e.g., Butyl Sepharose® 4 Fast Flow resin, Phenyl Sepharose™ HiSub, Capto™ Phenyl ImpRe, Capto™ Butyl ImpRes and Phenyl Sepharose™ High Performance resin from GE Healthcare, Toyopearl® Butyl-650 M and Toyopearl® Ether-650M resins from Tosoh Bioscience, POROS™ HIC resins (ethyl, Benzyl, Benzyl ultra) from Thermofisher Scientific.

In certain embodiments, the ligand of the HIC medium used in step a) is an alkyl group, a phenyl group, an ether group, or a diol group. In certain embodiments, the ligand of the HIC medium is an alkyl group such as a butyl group, a propyl group, an isopropyl group, a pentyl group, a hexyl group, or an octyl group. In certain preferred embodiments, the ligand of the HIC medium is a butyl group or a phenyl group. In more preferred embodiments, the HIC medium is composed of a base matrix material of hydroxylated methacrylic polymer beads that have been functionalized with a butyl ligand group. Commercially available HIC media comprising a butyl ligand include Butyl Sepharose™ 4 Fast Flow and Capto™ Butyl resins from GE Healthcare, Toyopearl® Butyl-650 M from Tosoh Bioscience and MacroPrep® HIC resins from Bio-Rad. Commercially available HIC media comprising a phenyl ligand include Phenyl Sepharose™ High Performance and Phenyl Sepharose™ HiSub.

In certain embodiments, the chromatography medium that may be used in step (a) is a medium comprising a ligand that comprises a hydrophobic group and an ionic group. The ligand may be coupled to a base matrix directly or via a spacer. Common base matrices of the chromatography medium include, but not limited to, agarose and hydrophilic polyvinyl ether. The hydrophobic group can be a phenyl group or a benzyl group. The ionic group can be a strong cation group (e.g., amine group), a weak cation group (e.g., dimethylamine group) or a combination thereof. Alternatively, the ionic group can be a strong anion group (e.g., sulfonic group), a weak anion group (e.g., carboxylic group) or a combination thereof. Such a chromatography medium may also be called a multimodal chromatography medium.

In certain embodiments, the hydrophobic group of the chromatography medium is a phenyl group or benzyl group and the ionic group of the chromatography medium is a strong cation group, weak cation group or a combination thereof. In certain embodiments, the hydrophobic ligand of the chromatography medium is a phenyl group or benzyl group and the ionic group of the chromatography medium is a strong anion group, a weak anion group or a combination thereof. In certain embodiments, the chromatography medium may further comprise a group that is a hydrogen bond donor or acceptor. In certain embodiments, the chromatography medium comprises an agarose base matrix and a ligand comprising a benzyl group and an amine group and may further comprises a hydrogen bond donor or acceptor. In certain embodiments, the chromatography medium comprises an agarose base matrix and a ligand comprising a phenyl group and a carboxylic group and may further comprises a hydrogen bond donor or acceptor. In certain embodiments, the chromatography medium comprises a hydrophilic polyvinyl ether base matrix and a ligand comprising a benzyl group, a sulfonic group and a carboxylic group, and may further comprises a hydrogen bond donor or acceptor. Multimodal chromatographic media are commercially available, e.g., multimodal Eshmuno® HCX resins from Millipore, and multimodal Capto™ adhere and Capto™ MMC resins from GE Healthcare.

The sample comprising a TNFR:Fc fusion protein is an aqueous solution having a salt concentration to allow the fusion protein to bind to a chromatography medium that comprises a ligand comprising a hydrophobic group. In certain embodiments, the chromatography medium is a HIC medium. In certain embodiments, the chromatography medium comprises a ligand comprising a hydrophobic group and an ionic group. TNFR:fc fusion proteins can bind to a chromatography medium that comprises a ligand comprising a hydrophobic group at a high salt concentration, which may be determined experimentally by a person of ordinary skill in the art. In certain embodiments, the sample has a salt concentration of from about 0.5 M to about 3 M. In certain embodiments, the sample has a salt concentration of from about 0.5 M to about 2.5 M. In certain embodiments, the sample has a salt concentration of from about 0.5 M to about 2 M. In certain embodiments, the sample has a salt concentration of from about 0.5 M to about 1.5 M. In certain embodiments, the sample has a salt concentration of from about 0.5 M to about 1 M. In certain embodiments, the sample has a salt concentration of from about 0.4 M to about 2 M, or from about 0.4 M to about 1.5 M, or from about 0.4 M to about 1 M. In certain embodiments, the sample has a salt concentration of about 0.4 M, about 0.6 M, about 0.8 M, about 1 M, about 1.2 M, about 1.4 M, about 1.6 M, about 1.8 M, about 2 M, or about 2.2 M. The salt concentration of the sample may be adjusted by, e.g., diluting the sample if the salt concentration is above the salt concentration under which the fusion protein binds to the chromatography medium, or adding additional salt if the salt concentration is below the salt concentration under which the fusion protein binds to the chromatography medium. Exemplary salts that may be used to adjust the salt concentration of the sample include ammonium sulfate, ammonium chloride, sodium sulfate, sodium chloride, sodium citrate, sodium acetate, sodium phosphate, potassium sulfate, potassium phosphate, potassium chloride, or a combination of two or more of these salts. Preferred salts that may be used to adjust the salt concentration of the sample include ammonium sulfate, ammonium chloride, sodium sulfate, sodium chloride, sodium acetate, sodium phosphate, sodium citrate or a combination of two or more of these salts.

The sample has a pH that does not negatively impact the TNFR:Fc fusion protein and/or its binding to the chromatography medium. Typically, the pH of the sample is in the range of from about 5.0 to about 8.5, preferably from about 6.5 to about 7.5. The pH of the sample may be adjusted using a buffering agent. Exemplary buffering agents include those that form phosphate buffers, acetate buffers and citrate buffers.

As used herein, the term "about," is understood to mean that there can be variations in a given value or range, including 20 percent, e.g., 10 percent, 5 percent, 4 percent, 3 percent, 2 percent, or 1 percent above or below of the stated value or range.

The chromatography medium may be washed after the binding of the TNFR:Fc fusion protein with a buffer before eluting the protein. Typically, buffers having a salt concentration and pH similar to that of the sample in the binding step described above may be used for washing the chrmatography medium. In certain embodiments, the washing buffer has a salt concentration of from about 0.5 M to about 1 M, or from about 0.5 M to about 1.5 M, or from about 0.5 M to about 2 M, or from about 0.5 M to about 2.5 M, or from about 0.5 M to about 3 M. In certain embodiments, the washing buffer has a salt concentration of from about 0.4 M to about 2 M, or from about 0.4 M to about 1.5 M, or from about 0.4 M to about 1 M. In certain embodiments, the washing buffer has a salt concentration of about 0.5 M, about 1 M, about 1.2 M, about 1.5 M, about 1.8 M, about 2 M, about 2.2 M, about 2.5 M, about 2.8 M, or about 3 M. In certain embodiments, the washing buffer has a salt concentration of about 0.4 M, about 0.6 M, about 0.8 M, about 1 M, about 1.2 M, about 1.4 M, about 1.6 M, about 1.8 M, about 2 M, or about 2.2 M. Exemplary salts that may be used in the washing buffer include ammonium sulfate, ammonium chloride, sodium sulfate, sodium chloride, sodium citrate, sodium acetate, sodium phosphate, potassium sulfate, potassium phosphate, potassium chloride, or a combination thereof preferred salts include ammonium sulfate, ammonium chloride, sodium sulfate, sodium chloride, sodium acetate, sodium phosphate, sodium citrate or a combination thereof.

The pH of the washing buffer is in the range of from about 5.0 to about 8.5, preferably from about 6.5 to about 7.5. In certain embodiments, the pH of the washing buffer is about 6.0, about 6.5, about 7.0, about 7.5 or about 8.0. Exemplary buffers include phosphate buffers, acetate buffers and citrate buffers. The washing buffer may comprise a buffering agent at a concentration of from about 10 mM to about 200 mM or from about 10 mM to about 100 mM.

Exemplary washing buffer includes 0.42 M sodium citrate, 0.05 M sodium phosphate, pH 6.5; 1.8 M ammonium sulfate, 0.1 M Sodium phosphate, pH 7.0; 1.0 M sodium sulfate, 0.1 M Sodium phosphate, pH 7.0; and 3.0 M sodium chloride, 0.1 M sodium phosphate, pH 7.0.

The TNFR:Fc fusion protein may be eluted from the chromatography medium in step b) using an elution buffer having a salt concentration that is lower relative to that of the washing buffer. The elution buffer typically has a salt concentration in the range of from about 0 to about 200 mM, or from 0 to about 150 mM, or from 0 mM to about 100 mM, or from 0 mM to about 50 mM, or from about 10 mM to about 30 mM. For example, the elution buffer can have a salt concentration of 0 mM, about 10 mM, about 20 mM, about 25 mM, about 30 mM, about 40 mM, about 50 mM, about 60 mM, about 70 mM, about 80 mM, about 90 mM, about 100 mM, about 120 mM, about 150 mM, about 170 mM, about 200 mM or about 250 mM. Exemplary salts that may be used in the elution buffer include ammonium sulfate, ammonium chloride, sodium sulfate, sodium chloride, sodium citrate, sodium acetate, sodium phosphate, potassium sulfate, potassium phosphate, potassium chloride, or a combination thereof; preferred salts include ammonium sulfate, ammonium chloride, sodium sulfate, sodium chloride, sodium acetate, sodium phosphate, sodium citrate, or a combination thereof.

The pH of the elution buffer is in the range of from about 5.0 to about 8.5, preferably from about 6.5 to about 7.5. In certain embodiments, the elution buffer has a pH of about 6.0, about 6.5, about 7.0, about 7.5, or about 8.0. Exemplary buffers that may be used in the elution buffer include phosphate buffers, acetate buffers and citrate buffers. The elution buffer may comprise a buffering agent at a concentration of from about 10 mM to about 200 mM or from about 10 mM to about 100 mM, e.g., about 10 mM, about 20 mM, about 30 mM, about 40 mM, about 50 mM, about 60 mM, about 70 mM, about 80 mM, about 90 mM, about 100 mM, about 120 mM, about 150 mM, about 170 mM or about 200 mM.

Exemplary elution buffer includes 0.025 M Sodium Phosphate, pH 6.5; 0.05 M Sodium Phosphate, pH 6.5; 0.1 M Sodium Phosphate, pH 7.0; about 0.25-0.35 M ammonium sulfate or sodium sulfate and about 0.01-0.2 M sodium acetate, sodium citrate, or sodium phosphate, pH of about 7; and about 0.5-0.7 M sodium chloride or ammonium chloride and about 10-200 mM sodium acetate, sodium citrate, or sodium phosphate, pH of about 7.

The elution buffer may comprise one or more additional reagents that weaken or disrupt the interaction between the TNFR:Fc fusion protein and the ligand(s) of the chromatography medium. Examples of such reagents include organic solvents such as glycols, acetonitrile and alcohols, detergents such as Triton X-100, urea, and salts that disrupt hydrophobic interactions (e.g., $MgCl_2$, $CaCl_2$, KI, and NaCNS). Exemplary alcohols include ethanol, which can be used in a concentration of up to about 10% v/v, and isopropanol, which can be used in a concentration of up to about 30% v/v. When Triton X-100 is added, it may be used at a concentration of from about 0.1% to about 1% v/v. Urea may be added to the elution buffer at a concentration of up to about 8 M.

In certain embodiments, the TNFR:Fc fusion protein is eluted in step b) using a gradient elution by applying a gradient of from 100% of a first solution to 100% of a second solution over a defined volume. In certain embodiments, the first solution is a washing buffer and the second solution is an elution buffer. Any of the washing buffers described above maybe paired with any of the elution buffers described above. Preferably, the first and second buffers have the same pH. More preferably, the first and second buffers are the same buffer. A typical gradient elution is performed over 10, 15 or 20 column volumes, during which fractions are collected and evaluated for product purity. In preferred embodiments, the gradient elution is performed over 10 column volumes. Gradient elution is an elution method well known and used in the art. See e.g., 31 P. Jandera J. Churácek, Gradient Elution in Column Liquid Chromatography: Theory and Practice ($1^{st}$ ed. 1985).

Exemplary gradient elution buffers include from 100% of a first solution of 0.5 M to about 2.5 M ammonium sulfate or sodium sulfate and about 0.01-0.2 M sodium acetate, sodium citrate, or sodium phosphate, pH of about 7, to 100% of a second solution of 0.25-0.35 M ammonium sulfate or sodium sulfate and about 0.01-0.2 M sodium acetate, sodium citrate, or sodium phosphate, pH of about 7; from 100% of a first solution of 0.5 M to about 3 M sodium chloride or ammonium chloride and about 0.01-0.2 M sodium acetate, sodium citrate, or sodium phosphate, pH of about 7, to 100% of a second solution of about 0.5-0.7 M sodium chloride or ammonium chloride and about 10-200 mM sodium acetate, sodium citrate, or phosphate, pH of about 7; from 100% of a first solution of 0.42 M Sodium Citrate, 0.05 M Sodium Phosphate, pH of about 6.5, to 100% of a second solution of 0.05 M sodium phosphate, pH of about 6.5; from 100% of a first solution of 1.87 M ammonium sulfate and 0.1M disodium phosphate pH of about 7.0, to 100% of a second solution of 0.1M sodium phosphate, pH of about 7.0; from 100% of a first solution of 1.0 M sodium sulfate and 0.1 M sodium phosphate, pH of about 7.0, to 100% of a second solution of 0.1 M Sodium phosphate, pH of about 7.0; and from 100% of a first solution of 3.0 M sodium chloride and 0.1 M Sodium Phosphate, pH of about 7.0, to 100% of a second solution of 0.1 M Sodium phosphate, pH of about 7.0. In a preferred embodiment, the TNFR:Fc fusion protein is eluted using a gradient elution by applying from 100% of a first solution of 0.42 M Sodium Citrate, 0.05 M Sodium Phosphate, pH of about 6.5, to 100% of a second solution of 0.05 M sodium phosphate, pH of about 6.5.

HIC can resolve a TNFR:Fc fusion protein into three peaks: Peak 1 is composed of truncated or clipped TNFR:Fc protein, e.g., arising from proteolytic cleavage, Peak 2 is composed of highly pure and biologically active TNFR:Fc protein, and Peak 3 is heterogeneous and is comprised of misfolded and aggregated protein along with other process related impurities (see U.S. Pat. No. 7,294,481, the disclosure related to the three peaks is incorporated herein by reference). The misfolded/aggregated TNFR:Fc protein, which is formed early in the cell culture process, represents a significant portion of product related impurities.

In certain embodiments, the TNFR:Fc fusion protein is eluted using a gradient elution wherein only Peak 2 fractions are collected and pooled together, and then subjected to next purification steps. This can be achieved by first establishing peak collection criteria for each of Peak 1, Peak 2 and Peak 3 during a gradient elution. Peak 2 fractions are collected using the collection criteria, pooled and then subjected to next purification steps. For example, in a gradient elution using a specific first and second solutions, each elution peak can be collected and analyzed by size exclusion chromatography (SEC) and/or analytical HIC. Peak collection criteria for each of Peak 1, Peak 2 and Peak 3 can be established based on the analytical results and the elution profile. See e.g., Example 1. In automated systems, criteria for collecting Peak 2 fractions may be established by methods known and used in the art, e.g., percentage peak max start and end collection criteria and loading based peak start and end collection criteria. See e.g., Strategies for Protein Purification Handbook (GE Healthcare), https://www.sigmaaldrich.com/content/dam/sigma-aldrich/does/Sigma-Aldrich/General_Information/1/ge-strategies-for-protein-purification.pdf (last visited Nov. 28, 2018) and Scopes, Robert K., Protein Purification Principles and Practice, 102-185 ($3^{rd}$ ed. 1994) (the parts for establishing percentage peak max start and end collection criteria and loading based peak start and end collection criteria are incorporated herein by reference). Thus, the use of a chromatography medium comprising a ligand comprising a hydrophobic group (e.g., HIC) can remove product related impurities such as Peak 1 and Peak 3 proteins and obtain highly pure Peak 2 TNFR:Fc protein.

In step c), the eluate from step b) is filtered through one or more viral filtration membranes to obtain a composition comprising the purified TNFR-Fc fusion protein. In certain embodiments, the eluate from step b) that is subjected to the filtration in step c) comprises less than about 5 wt % Peak 3 proteins or less than about 4 wt % Peak 3 proteins. In certain embodiments, the eluate from step b) that is subjected to the filtration in step c) comprises less than about 2 wt % Peak 3 proteins, less than about 1 wt % Peak 3 proteins or less than about 0.5 wt % Peak 3 proteins. In certain embodiments, the eluate from step b) that is subjected to the filtration in step c) comprises less than about 2 wt %, less than about 1 wt % Peak 3 proteins or less than about 0.5 wt % Peak 3 proteins and further comprises less than about 1 wt % of Peak 1 proteins.

The TNFR:Fc protein comprised in the eluate from step b) typically has a molecular weight of about 150 KD and/or a size of about 9 nm to about 12 nm in diameter. Viruses that may be present in the eluate from step b) include those having a size of about 100 nm in diameter (e.g., retrovirus) as well as viruses having a smaller size, e.g., parvovirus having a size of about 20 nm in diameter. Step c) can remove both types of viruses by selecting viral filtration membranes having a proper pore size or the approximate molecular weight (relative molecular mass) at which viruses are stopped by the filter while the fusion protein passes through (also known as known as pore size or molecular weight cut-off).

In certain embodiments, the one or more viral filtration membranes have a pore size of at or greater than about 15 nm. In certain embodiments, the one or more viral filtration membranes have a pore size of from about 15 nm to about 100 nm or from about 20 nm to about 100 nm. Representative viral filtration membranes which can be utilized in step c) include those formed from polyethersulfone (PES), polyarylsulphones, polysulfone, polyimide, polyamide, or polyvinylidenedifluoride (PVDF). In certain embodiments, the one or more viral filtration membranes are PES membranes, preferably hydrophilic asymmetric surface modified PES membranes. In certain embodiments, the one or more viral filtration membranes are PVDF membranes, preferably hydrophilic modified PVDF membranes. Such viral filtration membranes, including viral filtration membranes in special viral filter device formats, are commercially available, e.g., VIRESOLVE® membranes and RETROPORE™ membranes available from Millipore Corporation, Virosart®

HF, Virosart® CPV viral filter devices from Sartorius and Pegasus' from Pall Corporation. Viral filtration membranes can be supplied in different forms to suit either process development in small optiscale formats (e.g., VIRESOLVE® NFP, VIRESOLVE® NFR) to pilot scales in modus format all the way to cartridge format for large scale applications, and are available from manufacturers like Millipore Corporation, Pall Corporation (e.g., Pall Microdisc Capsules, Pall Mini Kleenpak™ Capsules), and Sartorius (e.g., Virosart® HF Mid-Scale/Lab-Scale Module).

The eluate from step b) being filtered in step c) has a protein concentration of from about 2 mg/mL to about 10 mg/mL, preferably from about 2 mg/mL to about 6 mg/mL.

Step c) may be performed by either a normal flow filtration (NFF) or a tangential flow filtration (TFF). In certain embodiments, step c) is performed by a NFF, which can be in a constant flow mode or a constant pressure mode. In constant flow NFF, the eluate from step b) is usually pumped around at a constant rate of flow on the retention side. The differential pressure generated across the virus filtration membrane(s) allows protein solution to permeate through the filter while the viruses are retained on the retentate side. Constant pressure NFF involves placing the eluate from step b) in a pressure vessel prior to filtration and pressing the solution through the virus filtration membrane(s) with the aid of a pressure source, suitably nitrogen (gas) or air. Alternatively, a pump could be used on the retentate side to filter the liquid through the virus filtration membrane(s) at a pre-determined flow rate.

In certain embodiments, the eluate from step b) is prefiltered prior to filtering through the one or more viral filtration membranes. Prefiltration can reduce flux decay and increase throughput in step c) by removing mis-folded and/or aggregated TNFR:Fc fusion proteins (e.g., Peak 3 proteins) present in the eluate from step b). In certain embodiments, the eluate from step b) is prefiltered using one or more adsorptive depth prefilters or synthetic depth prefilters. Exemplary adsorptive depth prefilters include those composed of diatomaceous earth, cellulose, activated carbon, high capacity diatomaceous earth metals and cellulose, or high capacity polyacrylic fiber and silica. Such adsorptive depth prefilters are commercially available from various companies, including, e.g., Clarisolve®, OptiScale® (e.g., OptiScale-40 Viresolve Prefilter in Capsule format), Millistak+®, Millistak+® HC (e.g., A1HC, and X0HC/X0SP), and Millistak+® HC Pro from Millipore Corporation, and Virosart® Max from Sartorius (available as Virosart® Max Minisart, Sartolab, Virosart® Max capsule and/or MidiCap®)

In certain embodiments, the eluate from step b) is prefiltered using one or more charged or surface modified microporous membranes. Such charged or surface modified microporous membranes include those composed of regenerated cellulose, polyethersulfone, polyarylsulphone, polysulfone, polyimide, polyamide or polyvinylidenedifluoride. Commercially available charged or surface modified microporous membranes may be obtained from various companies in various device formats, including Viresolve® Pro Shield and Viresolve® Pro Shield H prefilters from Millipore Corporation, and Pegasus™ Protect prefilter from Pall Corporation.

Methods disclosed herein may contain one or more additional purification steps selected from affinity chromatography, virus inactivation and diafiltration and ultrafiltration. Such one or more additional purifications may be performed before and/or after steps a) through c).

TNFR:Fc fusion proteins can be purified using the methods disclosed herein to a high degree of purity. Methods disclosed herein advantageously contain one polishing chromatographic step and have the advantages of achieving reduced flux decay and increased throughput in the virus filtration step. Another advantage of methods disclosed herein is that they have no virus breakthrough, especially during transition steps where there is a pause and/or pressure variation in the purification process.

The invention will be more fully understood by reference to the following examples. The examples should not, however, be construed as limiting the scope of the invention.

EXAMPLES

Example 1: HIC Method Establishment and Optimization

HIC method was established using a Toyopearl® Butyl-650 M column (10 mL, 1.1 cm ID×10 cm bed height). For optimal binding, etanercept filtered viral inactivated pool (FVIP) feed was conditioned to 0.42 M Sodium Citrate; 0.05 M Sodium Phosphate, pH 6.5 before loading on the column. After loading, bound protein was eluted using gradient elution over 10 column volume (CV), from 100% A buffer (0.42 M Sodium Citrate; 0.05 M Sodium Phosphate, pH 6.5) to 100% B buffer (0.05 M Sodium Phosphate, pH 6.5). The elution peak was fractionated and submitted for analytical size exclusion chromatography (SEC) and analytical HIC analyses. Based on the analytical results, and the elution profile, peak collection criteria for different etanercept species was established as follows: for Peak 1/Peak 2 (P1/P2): 43% to 56 B buffer; for Peak 2 (P2): 56% to 77% B buffer; for Peak 2/Peak 3 (P2/P3): 77% to 90% B buffer; for Peak 3 (P3): 90% to 100% B buffer+30 mL of 100% B buffer.

Figure 1:
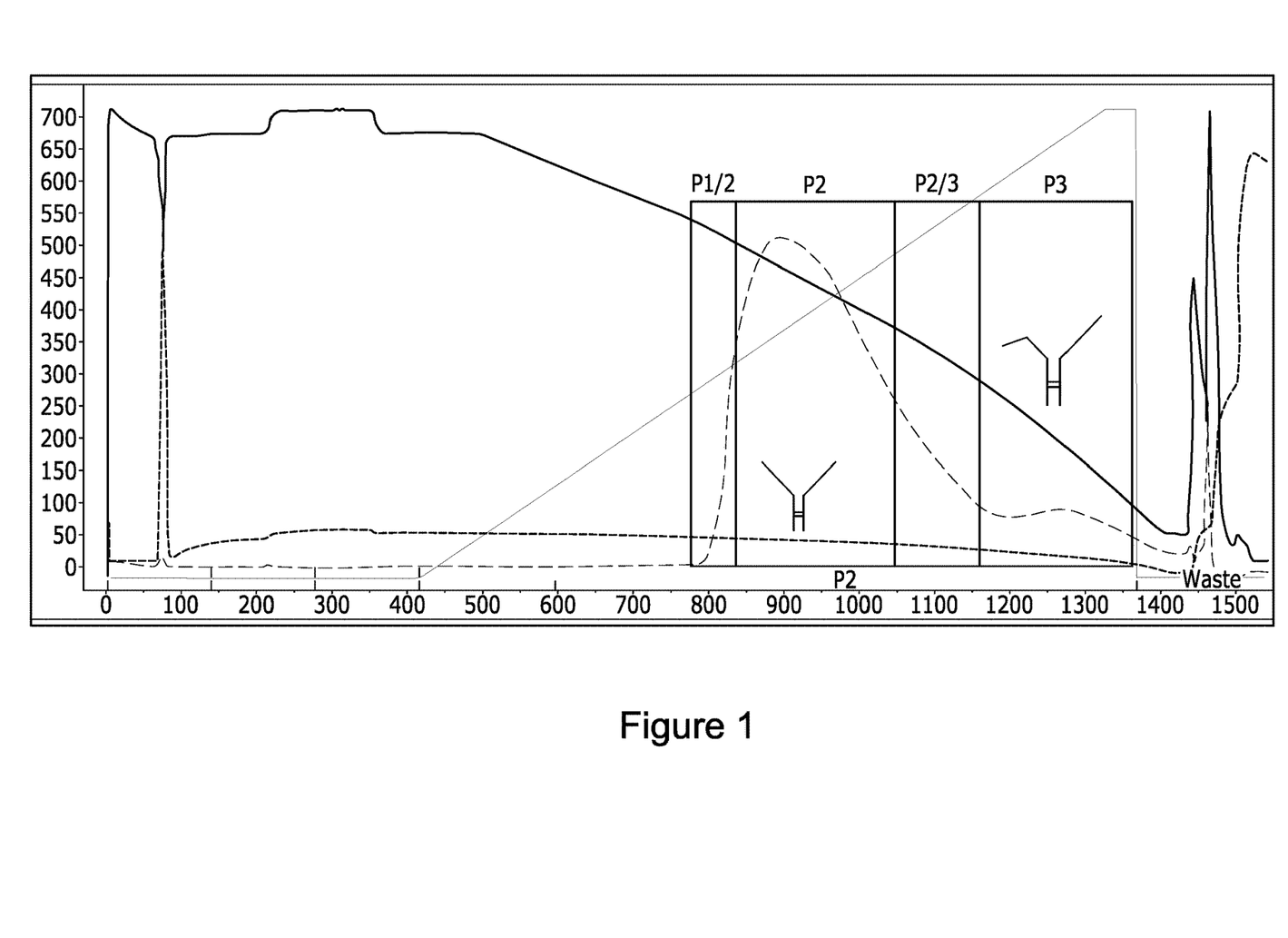
FIG. 1 shows the optimized peak cutting according to the peak collection criteria described in Example 1.

Next, etanercept FVIP was purified over a scaled up Toyopearl® Butyl-650 M column (25 mL, 1.6 cm 10×25 cm bed height). Elution pools comprised of P1/P2, P2, P2/P3, and P3 were collected according to the optimized peak cutting and collection criteria described above (see also FIG. 1). Table 1 shows the peak concentration and yield, and Table 2 shows the product quality data for the respective peaks. These results show that the established collection criteria are scalable across different column volumes. Product quality results revealed that the P2 pool and P3 pool obtained according to the peak cutting and collection criteria were of high purity (Table 2). One observation was that in comparison with the P2 pool, the P3 pool had higher amount of high molecule weight species (HMW) and host cell protein (HCP) (Table 2).

TABLE 1

Concentration and yield of different etanercept species from HIC

| Peak name | Concentration (mg/mL) | Yield (%) |
|---|---|---|
| P1/P2 | 1.73 | 40-41 |
| P2 | 1.22 | 44-45 |
| P2/3 | 0.3-0.36 | 7-9 |
| P3 | 0.30 | 6-7 |

TABLE 2

Product quality of HIC elution pools for P2 and P3

| Sample name | Concentration (mg/mL) | Analytical SEC (%) | | HCP (ppm) | Analytical HIC (%) | | |
|---|---|---|---|---|---|---|---|
| | | Main peak | HMW | | P1 | P2 | P3 |
| FVIP | 6.0 | 99.16 | 0.84 | 1753 | 0.74 | 82.88 | 16.38 |
| P2 | 1.23 | 99.54 | 0.46 | 137 | N/A | 100.00 | N/A |
| P3 | 0.25 | 97.18 | 2.83 | 1197 | N/A | 1.22 | 98.78 |

HCP: host cell protein
HMW: high molecule weight species

Figure 2:
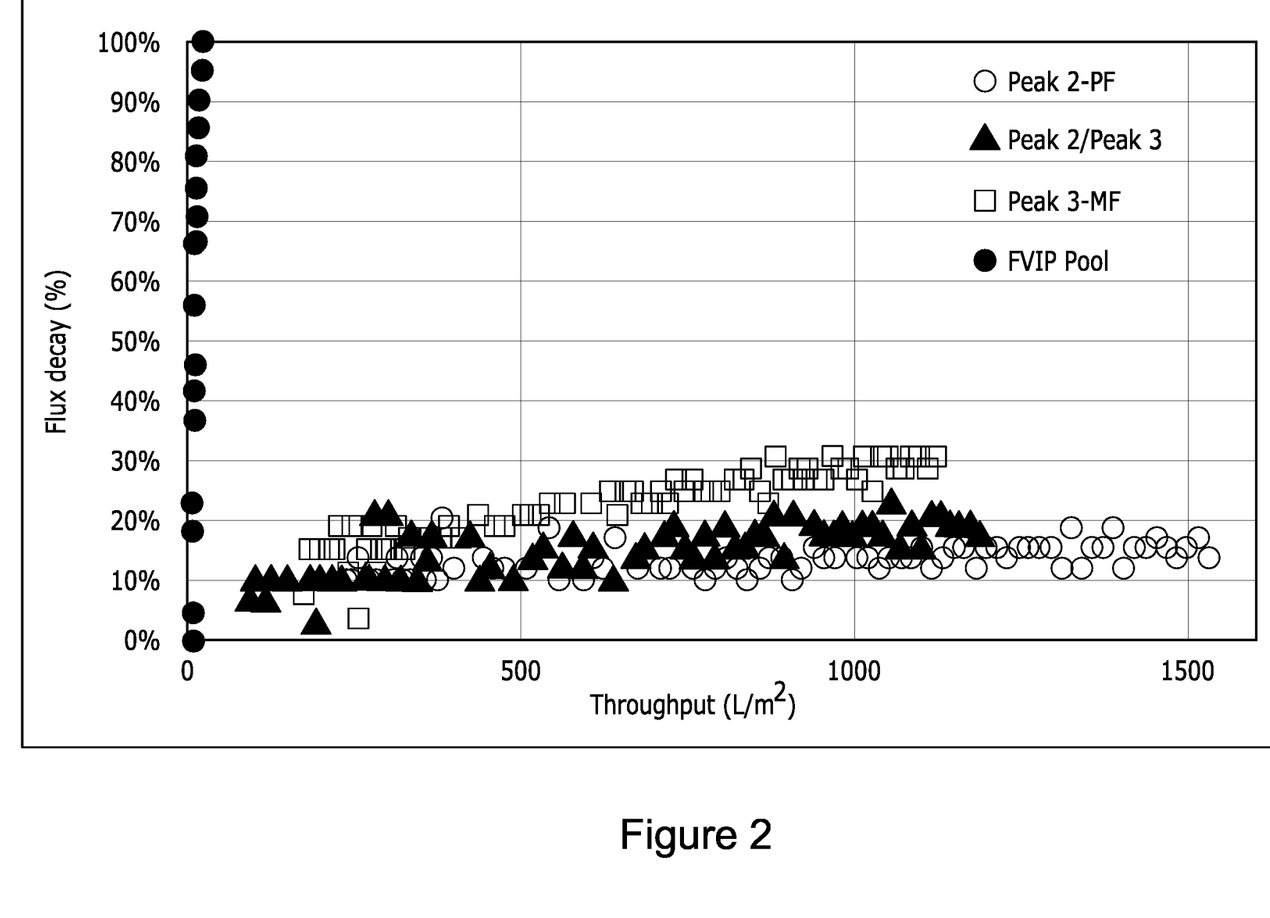
FIG. 2 shows flux decay and throughput of different samples using VireSolve® Pro (VPro) viral filters.

Example 2: Flux Decay Observed when Pure Peak Pools were Filtered Using VireSolve® Pro Membranes without Prefiltration Each of the samples comprised of FVIP, P2, P2/P3, and P3 pools obtained from Example 1 was filtered through a VireSolve® Pro (VPro) viral filter via a pressurized feed vessel. Flux decay of each sample was measured and shown in FIG. 2. The endpoint volumetric throughputs (L/m$^2$) reached were based on all available feed filtered through the respective devices. The FVIP pool, which comprises all three peaks, suffered a 100% flux decay at a throughput of 23 L/m$^2$ (FIG. 2). In contrast, significant filter throughput was obtained for the P2 and P3 pools purified by HIC. The P2 pool (active etanercept) reached a flux decay of 17% at a throughput of 1500 L/m$^2$. The P3 pool reached a relatively higher flux decay of 31% at a throughput of 1100 L/m$^2$ despite it had a lower protein concentration compared to that of the P2 pool (see Table 2). These data show that removal of misfolded species from the FVIP pool, e.g., by HIC and peak cutting, improved the throughput across viral filter. However, the P3 pool still experienced a relatively high flux decay, indicating that the presence of mis-folded and/or aggregated fusion proteins negatively impacted the downstream purification steps.

Example 3: Prefiltration Reduces Flux Decay

Figure 3:
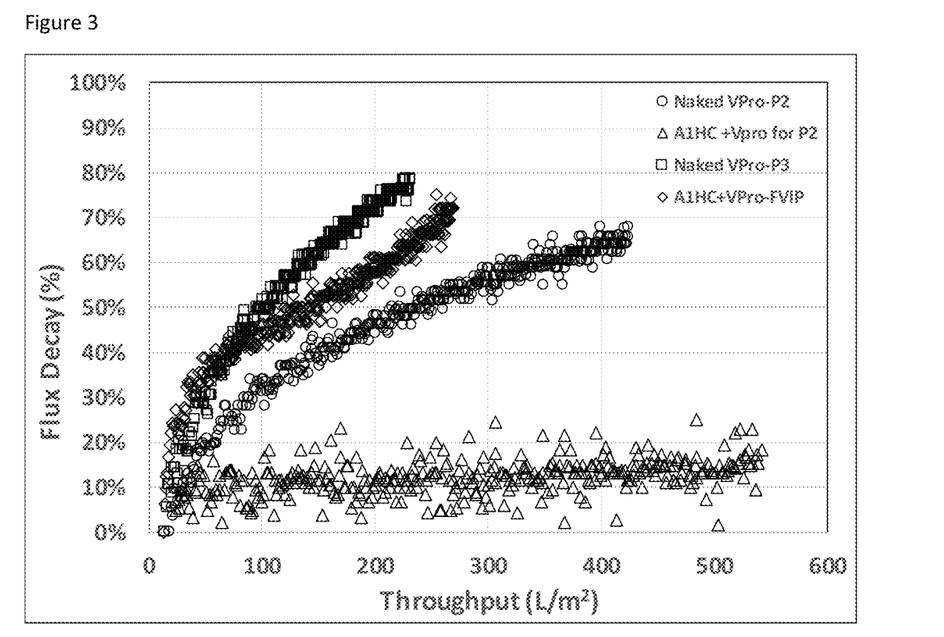
FIG. 3 shows flux decay and throughput of different samples using a combination of prefilter and viral filters ("A1HC/VPF+Vpro") or viral filters without prefilter ("Naked Vpro").

Samples comprised of FVIP, P2 pool or P3 pool were used in this experiment. The P2 and P3 pools had a protein concentration of 3.5 mg/mL and a pH of 7.2, and the FVIP had a protein concentration of 6.0 mg/mL and a pH of 7.2. The experimental setup is shown in Table 3 below. For virus filtration, the P2 pool was filtered through a combination of Viresolve® Prefilter (Optiscale®, OptiScale-40 Viresolve Prefilter, also called A1HC, in capsule format) and viral filtration membrane(s) (VireSolve® Pro) via a pressurized fee vessel. As a control, the FVIP pool was also filtered through a combination of Viresolve® Prefilter (Optiscale®, OptiScale-40 Viresolve Prefilter, also called A1HC, in capsule format) and viral filtration membrane(s) (VireSolve® Pro) via a pressurized feed vessel. In addition, the P2 and P3 pools were filtered through a VireSolve® Pro (VPro) viral filter via a pressurized feed vessel without a prefilter. Flux decay of each of the samples was shown in FIG. 3. Endpoints were based on when whole feed was filtered. In FIG. 3, samples filtered through a combination of Viresolve® Prefilter and viral filtration membrane(s) are labeled as "A1HC+Vpro," and samples filtered through viral filtration membrane(s) without prefilter are labeled as "Naked Vpro."

TABLE 3

Experimental setup

| Sample name | Protein concentration (mg/mL) | Viresolve ® Prefilter (Optiscale ®, OptiScale-40 Viresolve Prefilter A1HC) | Viral filter (VireSolve ® Pro) |
|---|---|---|---|
| FVIP | 6.0 | Yes | Yes |
| P2 | 3.5 | Yes | Yes |
| P2 | 3.5 | No | Yes |
| P3 | 3.5 | No | Yes |

As shown in FIG. 3, filterability of the P2 and P3 pools experienced a significant flux decay in the absence of prefiltration, the P2 pool had a flux decay of 60% at 400 L/m$^2$ whereas the P3 pool had an 80% flux decay at 220 L/m$^2$. The flux decay was worse compared to that seen in Example 2, likely due to the higher protein concentration of the P2 and P3 pools used in this experiment. In contrast, with the addition of a prefilter placed upstream of the viral filtration membrane(s), flux decay of the P2 pool was reduced to 16% at 400 L/m$^2$. The FVIP pool had a flux decay of 70% at 260 L/m$^2$ with the addition of a prefilter placed upstream of the viral filtration membrane. Overall, the use of prefilter improved the filterability of the P2 and FVIP pools by 44% and 25%, respectively. These data show that prefiltration significantly reduced flux decay and improved throughput of the virus filtration step.

Figure 4:
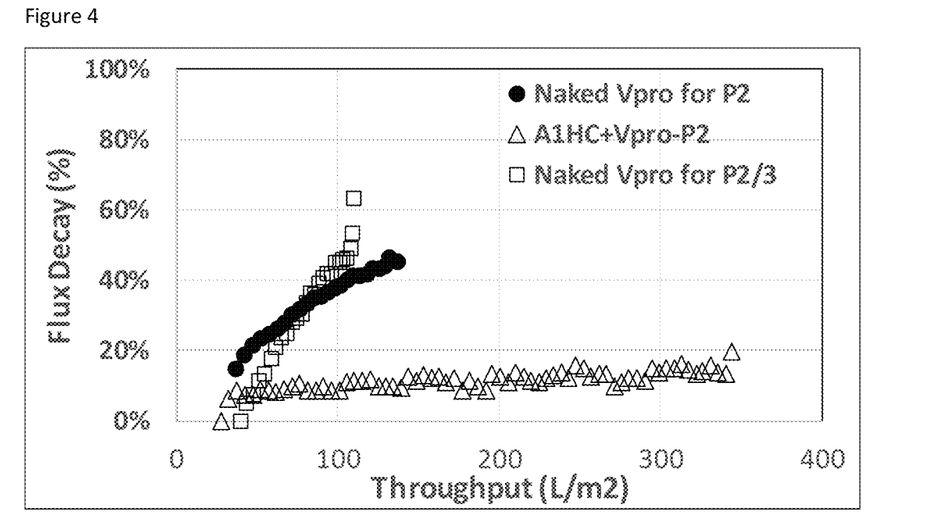
FIG. 4 shows flux decay and throughput of concentrated samples using a combination of prefilter and viral filters ("A1HC/VPF+Vpro") or viral filters without prefilter ("Naked Vpro").

Example 4: Effects of Higher Protein Concentration of Peak Pools on Flux Decay and Throughput P2 pool and P2/P3 pool were used in this experiment. The diafiltered P2 pool (protein concentration of about 7 mg/mL) was filtered over two different filter set-ups, one was filtered across viral filtration membranes (VireSolve® Pro) without a prefilter and the other was filtered across a combination of Viresolve® Prefilter (OptiScale-40 Viresolve Prefilter, A1HC) and viral filtration membranes (VireSolve® Pro). The P2/P3 concentrated and diafiltered pool (protein concentration of about 3 mg/mL) was also filtered through viral membranes without prefilter. Due to limited material, the P2/P3 pool was not concentrated to about 7 mg/mL. Results for this study are shown in FIG. 4. In FIG. 4, samples filtered through a combination of prefilter and viral filter are labeled as "A1HC+Vpro," and samples filtered through viral filter without a prefilter are labeled as "Naked Vpro."

As shown in FIG. 4, the higher concentration P2 pool (about 7 mg/mL) had a 48% flux decay at a throughput of 140 L/m$^2$ through viral filtration membranes without a prefilter, but the addition of a prefilter upstream of the viral filtration membranes had only a 10% flux decay at a similar throughput of 140 L/m$^2$. The addition of prefilter improved the filterability of the P2 pool by 38% at 140 L/m$^2$.

The concentrated P2/P3 pool (about 3 mg/mL) filtered through viral filtration membranes without a prefilter suffered a 50% flux decay at 110 L/m$^2$. This was understandable as the P2/P3 pool contained P3 (misfolded species) that can cause flux decay and reduce the membrane throughput (the pool was not tested for HIC P2 and P3 peak %).

To understand whether the process steps (e.g., concentrating of peak pools and prefiltration) had any impact on biological activity of etanercept, different pools obtained after HIC with the proposed process were submitted for bioassay. It was confirmed that the process steps did not have any negative impact on etanercept bioactivity.

The data from Examples 3 and 4 confirm that the removal of misfolded and/or aggregated species from the FVIP pool, e.g., by peak cutting and collection and/or prefiltration, improved the throughput across viral filtration membranes even at protein concentration as high as about 7 mg/mL.

All references cited in this application are incorporated by reference herein.

---

What is claimed:

1. A method for purifying a tumor necrosis factor receptor (TNFR):Fc fusion protein, comprising:
   (a) subjecting a sample comprising the TNFR:Fc fusion protein and at least one contaminant to a chromatography medium under conditions whereby the TNFR:Fc fusion protein binds to the chromatography medium,
   (b) eluting the TNFR:Fc fusion protein from the chromatography medium, and
   (c) filtering the eluate from (b) through
      (i) one or more adsorptive prefilters; or
      (ii) one or more charged or surface modified microporous membranes; and
   (d) filtering the eluate from (c) through one or more viral filtration membranes to obtain the purified TNFR:Fc fusion protein, wherein the chromatography medium (i) is a hydrophobic interaction chromatography (HIC) medium or (ii) comprises a ligand comprising a hydrophobic group and an ionic group.

2. The method of claim 1, wherein the TNFR:Fc fusion protein is etanercept.

3. The method of claim 1, wherein the chromatography medium is a HIC medium and the ligand of the HIC medium is an alkyl group, a phenyl group, an ether group, or a diol group.

4. The method of claim 3, wherein the chromatography medium is a HIC medium and the ligand of the HIC medium is a butyl group or a phenyl group.

5. The method of claim 4, wherein the HIC medium is composed of hydroxylated methacrylic polymer resins functionalized with a butyl ligand group.

6. The method of claim 1, wherein the chromatography medium comprises a ligand comprising a hydrophobic group and an ionic group and
   a) the hydrophobic group is a phenyl group or a benzyl group, and the ionic group is a strong cation group, a weak cation group, or a combination thereof; or
   b) the hydrophobic group is a phenyl group or a benzyl group, and the ionic group is a strong anion group, a weak anion group, or a combination thereof.

7. The method of claim 1, wherein the chromatography medium comprises a ligand comprising a hydrophobic group and an ionic group and the ligand comprises 1) a benzyl group and an amine group, 2) a phenyl group and a carboxylic group, or 3) a benzyl group, a sulfonic group and a carboxylic group.

8. The method of claim 1, wherein the sample has a salt concentration of from about 0.4 M to about 2 M and a pH of from about 5.0 to about 8.5.

9. The method of claim 1, wherein the TNFR:Fc fusion protein is eluted using a gradient of: from 100% of a first solution having a salt concentration of from about 0.4 M to about 2 M, to 100% of a second solution having a salt concentration of from 0 mM to about 100 mM.

10. The method of claim 9, wherein the first solution and the second solution each comprises a salt selected from ammonium sulfate, ammonium chloride, sodium sulfate, sodium chloride, sodium citrate, sodium acetate, sodium phosphate, potassium sulfate, potassium phosphate, and potassium chloride.

11. The method of claim 9, wherein the first and second solutions have the same pH in the range of from about 5.0 to about 8.5.

12. The method of claim 9, wherein the first and second solutions comprise the same buffer selected from a phosphate buffer, an acetate buffer, or a citrate buffer.

13. The method of claim 9, wherein the first and the second solutions each comprises a buffering agent at a concentration of from about 10 mM to about 200 mM.

14. The method of claim 9, wherein the first solution comprises 0.42 M Sodium Citrate, 0.05 M Sodium Phosphate, and a pH of about 6.5, and the second solution comprises 0.05 M Sodium Phosphate, and a pH of about 6.5.

15. The method of claim 1, wherein the eluate from step (b) that is subjected to the filtration in step (d) comprises less than about 1 wt % of HIC Peak 3, or the eluate from step (b) that is subjected to the filtration in step (d) comprises less than about 1 wt % of HIC Peak 3 and less than about 1 wt % of HIC Peak 1.

16. The method of claim 1, wherein the eluate being filtered in step (d) has a protein concentration of from about 2 mg/mL to about 10 mg/mL.

17. The method of claim 1, wherein the pore size of the one or more viral filtration membranes is from about 20 nm to about 100 nm.

18. The method of claim 1, wherein the one or more viral filtration membranes are polyethersulfone (PES) membranes or polyvinylidene fluoride (PVDF) membranes.

19. The method of claim 18, wherein the PES membrane is a hydrophilic asymmetric surface modified PES membrane, and the PVDF membrane is a hydrophilic modified PVDF membrane.

20. The method of claim 1, wherein the adsorptive pre-filters are composed of diatomaceous earth metals and cellulose, activated carbon, high capacity diatomaceous earth metal and cellulose, or High capacity polyacrylic fiber and silica.

21. The method of claim 1, wherein the charged or surface modified microporous membranes are composed of regenerated cellulose, polyethersulfone, polyarylsulphone, polysulfone, polyimide, polyamide, or polyvinylidenedifluoride.

* * * * *

SEQUENCE LISTING

<160> NUMBER OF SEQ ID NOS: 1

<210> SEQ ID NO 1
<211> LENGTH: 467
<212> TYPE: PRT
<213> ORGANISM: Artificial Sequence
<220> FEATURE:
<223> OTHER INFORMATION: TNFR:Fc fusion proteins

<400> SEQUENCE: 1

```
Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320
```

```
Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465
```